United States Patent
Flohr et al.

(10) Patent No.: US 9,907,529 B2
(45) Date of Patent: Mar. 6, 2018

(54) PATIENT-DEPENDENT OPTIMIZATION OF THE AMOUNT OF CONTRAST MEDIUM

(71) Applicant: Siemens Aktiengesellschaft, Munich (DE)

(72) Inventors: Thomas Flohr, Uehlfeld (DE); Bernhard Schmidt, Fuerth (DE)

(73) Assignee: Siemens Aktiengesellschaft, Munich (DE)

( * ) Notice: Subject to any disclaimer, the term of this patent is extended or adjusted under 35 U.S.C. 154(b) by 196 days.

(21) Appl. No.: 14/620,381

(22) Filed: Feb. 12, 2015

(65) Prior Publication Data

US 2015/0238160 A1    Aug. 27, 2015

(30) Foreign Application Priority Data

Feb. 26, 2014 (DE) .................. 10 2014 203 463

(51) Int. Cl.
| | | |
|---|---|---|
| *A61B 6/00* | (2006.01) | |
| *A61B 6/03* | (2006.01) | |
| *G06T 5/00* | (2006.01) | |

(52) U.S. Cl.
CPC .............. *A61B 6/544* (2013.01); *A61B 6/032* (2013.01); *A61B 6/4266* (2013.01); *A61B 6/481* (2013.01);
(Continued)

(58) Field of Classification Search
CPC ......... A61B 6/544; A61B 6/032; A61B 6/484; A61B 6/481; A61B 6/5294; G06T 5/001
See application file for complete search history.

(56) References Cited

U.S. PATENT DOCUMENTS

| 8,537,969 B2 | 9/2013 | Allmendinger |
|---|---|---|
| 2003/0108149 A1 | 6/2003 | Tsuyuki |

(Continued)

FOREIGN PATENT DOCUMENTS

| CN | 1426762 A | 7/2003 |
|---|---|---|
| CN | 1488317 A | 4/2004 |

(Continued)

OTHER PUBLICATIONS

German Office Action mailed Oct. 15, 2014.
Chinese Office Action dated Feb. 28, 2017, in Chinese Application No. 201510031929.5.

*Primary Examiner* — Courtney Thomas
(74) *Attorney, Agent, or Firm* — Harness, Dickey & Pierce, P.L.C.

(57) ABSTRACT

A method and an apparatus are disclosed for patient-dependent optimization and reduction of the contrast medium amount. An embodiment includes provisioning patient-specific data, containing information about a patient cross-section relevant for the imaging measurement; establishing CT values and/or CNR values of a contrast medium to be expected for at least one region of interest of the patient for different candidate settings of x-ray source arrangement and/or of an image reconstruction device; determining a relevant candidate contrast medium amount for the different candidate settings, which would lead to a CT value or CNR value of the contrast medium which corresponds to the CT value or CNR value of the contrast medium at the reference setting of the x-ray source arrangement and/or image reconstruction device; and displaying an optimum relative candidate contrast medium amount and of the associated candidate setting.

20 Claims, 1 Drawing Sheet

(52) U.S. Cl.
CPC .............. *A61B 6/482* (2013.01); *A61B 6/484* (2013.01); *A61B 6/5294* (2013.01); *A61B 6/545* (2013.01); *G06T 5/001* (2013.01)

(56) References Cited

U.S. PATENT DOCUMENTS

| | | |
|---|---|---|
| 2004/0114706 A1 | 6/2004 | Ikeda et al. |
| 2008/0027309 A1 | 1/2008 | Hempel et al. |
| 2011/0313287 A1 | 12/2011 | Nemoto |
| 2012/0101376 A1 | 4/2012 | Allmendinger |
| 2012/0236995 A1* | 9/2012 | Eusemann ............... A61B 6/03 378/108 |
| 2013/0010922 A1 | 1/2013 | Taguchi et al. |
| 2014/0005533 A1 | 1/2014 | Grasruck et al. |

FOREIGN PATENT DOCUMENTS

| | | |
|---|---|---|
| CN | 102551778 A | 7/2012 |
| CN | 102670225 A | 9/2012 |
| CN | 102695454 A | 9/2012 |
| CN | 103429156 A | 12/2013 |
| DE | 102005052368 A1 | 5/2007 |
| DE | 102006032991 A1 | 1/2008 |
| DE | 102008045633 A1 | 3/2010 |
| DE | 102011083727 A1 | 4/2013 |

\* cited by examiner

PATIENT-DEPENDENT OPTIMIZATION OF THE AMOUNT OF CONTRAST MEDIUM

PRIORITY STATEMENT

The present application hereby claims priority under 35 U.S.C. § 119 to German patent application number DE 102014203463.9 filed Feb. 26, 2014, the entire contents of which are hereby incorporated herein by reference.

FIELD

At least one embodiment of the invention generally relates to a method and/or an apparatus for patient-dependent optimization and reduction of the amount of contrast medium, especially in computed tomography, and/or a control and processing unit and/or also an x-ray imaging device, especially computed tomography device.

BACKGROUND

Non-invasive presentation of internal body structures and organs by way of computed tomography or other x-ray imaging methods is a widely-used method in medical diagnostics. In such diagnostics a high contrast between bones and soft tissue can be obtained. However contrast between different soft tissues, because of small differences in absorption, is only suitable for diagnostics to a restricted extent.

Therefore contrast media are applied to increase the contrast of specific body structures or body fluids. These contain elements strongly absorbing x-ray radiation in order to obtain a high image contrast to the surrounding tissue with low absorption.

In radiological imaging by way of x-ray radiation, contrast media (CM) containing iodine are used nowadays for presenting body fluids, organs and pathological processes. Because of its absorption properties iodine is not the optimum element for contrast enhancement in x-ray diagnostics for tube voltages higher than 80 kV. This especially applies to CT, in which tube voltages of up to 140 kV are used nowadays. In the energy range of the x-ray radiation used the x-ray density of contrast media increases with the atomic number of the contrasting element. The use of contrast media of high atomic number is therefore especially suitable for CT, wherein, as well as the lanthanides, hafnium, rhenium, tantalum or tungsten are used as absorbing elements. In the use of each of these contrast media however, despite the high safety profile, undesired side-effects can occur.

Despite this, the largest proportion of contrast media currently used for x-ray diagnostics is based on iodine as the main x-ray attenuating component. Current device technology is optimized for this. In the choice of element for contrast media the element should exhibit an atomic number that is as high as possible, since the x-ray absorption increases strongly with the atomic number. The design of x-ray devices does not simply lie in the softest possible x-ray radiation producing the best contrast between water and the contrast medium.

The quality of the presentation or demarcation of two different tissue types or of tissue containing contrast medium from surrounding contrast-medium-free tissue can be described quantitatively by the contrast-to-noise ratio (CNR) between the two tissue types or between tissue with and without contrast medium. This is given by the CT value (also referred to as the attenuation value or HU value; HU=Hounsfield Unit) of the contrast medium and also the CT value of the neighboring contrast-medium-free tissue in relation to the image noise in this area.

The x-ray radiation used in radiological diagnostics is polychromatic, i.e. the wavelengths and thus the energies of the photons produced by an x-ray tube are not identical. The energy spectrum or photon spectrum of the x-ray radiation emitted by an anode is predetermined by the anode material and the tube voltage used. Tungsten anodes are used almost exclusively today in CT. Within the irradiated object the photon spectrum emitted is constantly changing since the absorption of x-ray radiation is energy-dependent and an overlaying with scattered photons occurs.

These interrelationships are complex and cannot be described by simple mathematical relationships. Thus the photon spectrum changes for example as a function of the irradiated volume, the penetration depth and the tissue composition. The x-ray density of a CM and thus the image signal is determined by the attenuation coefficient of the contrasting element, its local concentration, in combination with the photon spectrum at the point of physical interaction. Thus the actual irradiated thickness of the body of a patient is to be taken into account accordingly.

Because of the high probability of interaction between low-energy photons and tissue, the low energy components in the photon spectrum (in the range smaller than 50 keV), although they lead to a dose entry, they only make a small contribution to image generation. Thus, the use of photon energies of less than 50 keV leads with the same radiation dose to an increase in image noise.

Simulations show that, to obtain a high soft tissue contrast in CT under the condition of the minimum dose, photon energies ranging between 70 and 140 keV must be used. This is compared to contrast-medium-supported CT, in which the photon energies between 35 and 70 keV deliver the highest CNR-to-dose ratio. This contrast between native and contrast-medium-supported CT recordings is attributable to the spectral absorption characteristic of iodine.

The high absorption of iodine in the range of between 33 keV up to around 70 keV overcomes the unfavorable dose effect of low energy photons in such cases. With contrast media with elements of a higher atomic number, such as the lanthanoides, Hf, Ta or Re, the optimum energy range of the contrast-medium-supported CT shifts to higher energies in the range of between 60 and 140 keV and is thus practically identical to the optimum energy range for soft tissue contrast.

The amount of contrast medium administered to the patient depends on the planned examination and on the anatomy/physiology of the patient. For example a usual dose is 0.5 g of iodine per kg body weight for examinations of the parenchymatous stomach organs. The object is to achieve a contrast increase desired by the user in the relevant organs, in order thus to create a specific ratio of contrast and image noise (contrast-to-noise ratio CNR) in the CT images. Because contrast media can have undesired side-effects, the aim of many CT examinations, especially of older patients and patients with impaired kidney functions, is to minimize as far as possible the amount of contrast medium for the patient in order to achieve the objective of the examination.

According to the prior art, the amount of contrast medium administered to the patient is made dependent, as part of a contrast medium protocol, on an examination protocol (i.e. the type or objective of the intended examination, e.g. CT angiography, or examination of parenchymatous organs) and on the anatomy/physiology of the patient (height, weight, BMI, age etc.). The major parameters concentration, amount and flow rate of the contrast medium—depending on the planned examination and depending on patient characteristics such as height, weight etc., are mostly determined empirically by the doctor (e.g. 0.5 g iodine per kg of body weight for examinations of the parenchymatous organs). In the interim there have been also semi-automatic or fully automatic programs in accordance with the prior art which model the physiology and the circulation of the patient individually from parameters such as weight, size, heart performance, ejection rate of the heart etc., in order to obtain recommendations for a contrast medium protocol from said parameters.

The publication DE 102005052368 A1 from the same applicant discloses an x-ray system for creating diagnostic presentations of a patient with at least:
one x-ray tube for creating an x-ray bundle of x-rays with an energy spectrum for scanning the patient,
a detector for measuring the attenuation of the x-ray radiation as it passes through the patient,
an application unit for administering contrast medium for improving contrast in the x-ray imaging of the patient,
a control and processing unit for controlling the x-ray system and for creating the x-ray images of the patient with the aid of stored and executed computer programs, wherein
the x-ray system has an option for selecting different operating parameters at least in relation to the energy spectrum of the x-ray radiation used, wherein
the x-ray system has a selection device, which after direct or indirect specification of the parameters examination volume on one hand and tissue structure on the other hand, specifies at least a combination of contrast media and energy spectrum of the x-ray radiation for the examination with which an optimum contrast-to-noise ratio is achieved in the examination area for the smallest radiation dose and contrast medium load.

Here the contrast-to-noise ratio (CNR) is defined as the optimization target, so that a combination of contrast medium and energy spectrum of the x-ray radiation optimized in this way is obtained. No minimization of a contrast medium load is possible with this however since the radiation dose for the body of the patient or the test item is included in the calculation which thus likewise cannot achieve a minimum.

SUMMARY

At least one embodiment of the present invention is directed to a method, during recording of an x-ray image with the incorporation of contrast medium in the area to be displayed, to improve or even optimize the contrast medium dose, i.e. the contrast medium concentration in the body of the patient or in the test item, preferably to minimize it, wherein a sufficiently high CT value and/or CNR value of the tissue containing contrast medium is to be guaranteed.

A method and a device are disclosed, along with a control and processing unit and an x-ray imaging unit, especially a CT unit.

In accordance with at least one embodiment of the invention the method comprises:
Step a): Provision of patient-specific data which at least contains information about a relevant cross-section of the patient to be irradiated during an imaging measurement.
Step b): Establishing expected CT values or CNR values of a predetermined number of contrast media for at least one region of interest (ROI) of the patient for different candidate settings of an x-ray source arrangement and/or an image reconstruction device for reconstruction of monoenergetic image data from multi-energy measurements, relative to a CT value or CNR value for this region of interest ROI for a reference setting of the x-ray source arrangement and/or of the image reconstruction device as a function of the patient-specific data.
Step c): Determination of a relevant candidate contrast medium amount in each case, e.g. in percent, for the different candidate settings of the x-ray source arrangement and/or the image reconstruction device, which would lead to a CT value or CNR value of the contrast medium for the region of interest (ROI) which corresponds to the CT value or CNR value of the contrast medium at the reference setting of the x-ray source arrangement and/or image reconstruction device.
Step d): Display of an optimum candidate contrast medium amount, e.g. the minimum relative amount and the associated candidate setting for the x-ray source arrangement and/or the image reconstruction device.

At least one embodiment of the inventive device includes at least the following features:
a) An interface for provision of patient-specific data, which contains at least information about a patient cross-section relevant during the imaging measurement,
b) A CT value establishing unit for establishing expected CT values of a predetermined contrast medium for at least one region of interest of the patient at different candidate settings of an x-ray source arrangement and/or an image reconstruction device for reconstruction of monoenergetic image data from multi-energy measurements relative to a CT value for this region of interest at a reference setting of the x-ray source arrangement and/or the image reconstruction device as a function of the patient-specific data,
c) A contrast medium amount determination unit for determining in each case a relative candidate contrast medium amount for the different candidate settings which would lead to a CT value of the contrast medium which corresponds to the CT value of the contrast medium at the reference setting of the x-ray source arrangement and/or image reconstruction device, and
d) A display unit for displaying an optimum relative candidate contrast medium amount and the associated candidate setting.

Furthermore, at least one embodiment of the present invention also protects a control and processing unit for an x-ray imaging device, especially computed tomography device, operating in accordance with the aforementioned method and/or containing the aforementioned device.

Furthermore, at least one embodiment of the present invention also protects an x-ray imaging device, especially computed tomography device, operating in accordance with the aforementioned method and/or containing the aforementioned control and processing unit.

In particular major parts of at least one embodiment of the inventive device, e.g. the interface, the CT value establishing unit and the contrast medium amount determination unit can also be embodied in the form of software components.

At least one embodiment of the invention thus also includes a computer program which is able to be loaded directly into a memory of a control and processing unit of an x-ray imaging device, especially a computed tomography device, with program code in order to perform all steps of the inventive method when the program is executed in the control and processing unit. The control and processing unit in such cases can especially also be constructed as a system of a number of network computers or processors. A software realization has the advantage that existing x-ray imaging devices or computed tomography devices realized with suitable programmable processors and memories can be modified in a suitable manner by implementation of the program in order to operate in the inventive manner.

Further especially advantageous embodiments and developments of the invention emerge from the dependent claims as well as the description given below, wherein the independent claims of one claim category can be developed similarly to the dependent claims of another claim category. Likewise individual features or groups of features of different example embodiments of the invention can also be combined into new example embodiments.

BRIEF DESCRIPTION OF THE DRAWINGS

The invention will be explained once again in greater detail below with reference to the enclosed FIGURE on the basis of an example embodiment.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the FIGURES.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the FIGURE. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the FIGURES. For example, two FIGURES shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the FIGURES. It will be understood that the spatially relative terms are intended to encompass different orientations of the device in use or operation in addition to the orientation depicted in the FIGURES. For example, if the device in the FIGURES is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In accordance with at least one embodiment of the invention the method comprises:

Step a): Provision of patient-specific data which at least contains information about a relevant cross-section of the patient to be irradiated during an imaging measurement.

Step b): Establishing expected CT values or CNR values of a predetermined number of contrast media for at least one region of interest (ROI) of the patient for different candidate settings of an x-ray source arrangement and/or an image reconstruction device for reconstruction of monoenergetic image data from multi-energy measurements, relative to a CT value or CNR value for this region of interest ROI for a reference setting of the x-ray source arrangement and/or of the image reconstruction device as a function of the patient-specific data.

Step c): Determination of a relevant candidate contrast medium amount in each case, e.g. in percent, for the different candidate settings of the x-ray source arrangement and/or the image reconstruction device, which would lead to a CT value or CNR value of the contrast medium for the region of interest (ROI) which corresponds to the CT value or CNR value of the contrast medium at the reference setting of the x-ray source arrangement and/or image reconstruction device.

Step d): Display of an optimum candidate contrast medium amount, e.g. the minimum relative amount and the associated candidate setting for the x-ray source arrangement and/or the image reconstruction device.

Since, as described above, the CNR value is based in any event on the CT value, only the CT value will be mentioned below as an example for both options. However this is not intended to restrict embodiments of the invention to the calculation of CT values.

Re. Step a): This patient-specific data can be obtained from analog and/or digital x-ray images already prepared in previous examinations but can also be obtained from simple photo or video data or from simple anatomical determinations and their calculations of the patient, such as for example the extent of the head, chest cavity, the midriff, the stomach, the hips, the extremities, the overall height and the weight and the resulting BMI of the patient, etc.

Re. Step b): The CT values to be expected are especially averaged values over a defined region, for example an ROI, i.e. a region of the patient to be examined. Naturally the CT values can be not just averaged values but also weighted CT values.

It is especially preferred for at least one embodiment of the inventive method to be used, not just for a single CM, e.g. iodine, but for a plurality of selected CMs. Thus not only the optimum/minimum amount or concentration can then be used but also the appropriate CM for the purpose, e.g. bromine compounds.

The term "candidate settings" here can mean on the one hand the setting of the parameters of the x-ray source arrangement, namely preferably the x-ray voltage which is correlated with the x-ray photon energy and/or the x-ray current which is correlated linearly with the x-ray dose. In such cases the establishing or calculation of the CT values can be carried out for individual discrete setting values or the CT values of the contrast medium are calculated for (almost) all possible selectable values of a parameter (e.g. voltage or current), i.e. the one (quasi-) continuous function of the relative CT value is determined depending on the parameters concerned.

On the other hand the term "candidate setting" means here that monoenergetic image data with specific (candidate) parameter values will be created by means of an image reconstruction device from the image data which was created with different x-ray spectra or average x-ray energies. Provided a multi-energy measurement (especially dual-energy measurement) is carried out, namely as an alternative or in addition for the settings of at least one of the x-ray sources itself, the CT values can also be determined for different candidate settings of the image reconstruction device for reconstruction of monoenergetic image data from the multi-energy measurements. Such monoenergetic image data is mixed images from the image datasets which have been recorded at two or more different x-ray voltage is or average x-ray energies and correspond to the image data as were created during a measurement with a (virtual) x-ray energy.

Methods for creating such mixed images or monoenergetic images from datasets of different x-ray energies are known from the publications DE 10 2008 045 633 A1 and DE 10 2011 083 727 A1 (the entire contents of each of which are hereby incorporated herein by reference) attributable to the same applicant and are included in their full scope in relation to the creation of such mixed images, so that any further explanations can be dispensed with here.

In principle any given value can serve as a "reference setting". A standard setting of the x-ray source(s), e.g. a standard x-ray energy with the standard x-ray voltage of e.g. 120 kV is used here as the "reference setting", which then creates a standard reference CT value in the ROI of e.g. 200 HU (one of 4096 Hounsfield gray scale values between minus 1024 HU and plus 3071 HU), as a function of the patient-specific data.

This standard x-ray energy with a standard x-ray voltage is then not a real voltage that can be set for a multi-energy measurement, but a virtually-created, especially computed voltage of the image reconstruction device, as a function of the patient-specific data.

The candidate settings can, as stated, involve the x-ray voltage of the x-ray source (or of the x-ray tubes) which corresponds to the x-ray energy. The candidate settings can however also, as an alternative or in addition, involve the x-ray current which corresponds to the x-ray dose. Since the x-ray source can also involve an x-ray source with a number of x-ray spectra such as e.g. in a dual-energy/multi-energy computed tomography device or a number of x-ray sources, such as e.g. a so-called dual-source computed tomography device, the general term "x-ray source arrangement" is used here so that said term means at least one or even more x-ray sources which operate with one or more x-ray spectra or one or more average x-ray energies.

Re. Step c): The relative candidate contrast medium amount in this case is that candidate contrast medium amount by which percentage or by which factor the contrast medium amount could be changed so as to lead to a CT value of the contrast medium which corresponds to the CT value of the contrast medium at the reference setting of the x-ray source arrangement.

Re. Step d): If the minimum relative candidate contrast medium amount is displayed then a check can be made beforehand whether the assigned candidate setting of the x-ray source arrangement is permitted or not. If not then a relative candidate contrast medium amount closest to the minimum relative candidate contrast medium amount can be selected as the optimum relative candidate contrast medium amount.

With widely used CT contrast media, such as iodine for example, the x-ray absorption strongly depends on the energy of the x-ray radiation. As the energy of the x-ray radiation decreases the x-ray absorption of iodine sharply increases for example—thus the CT value increases (the measured values of the absorbed x-ray radiation and thus the gray scale value) of organs through which blood is flowing in the CT image and the contrast to their environment becomes greater. The energy of the x-ray radiation at which the absorption of the contrast medium is measured in a CT examination and which ultimately determines for a given contrast medium protocol the CT value of the contrast medium and thus the image contrast of organs with blood flowing through them in the CT image can be modified in accordance with at least one embodiment of the invention in the following ways:

A first preferred solution is as follows: By changing the tube voltage used during the CT examination, which generally lies between 70 and 140 kV and can be set by the user (e.g. 80 kV, 100 kV, 120 kV, or 140 kV). For each tube voltage a different average energy of the x-ray spectrum is produced.

A second preferred solution is as follows: Through dual-energy CT examinations (two x-ray tube units and two x-ray sensor arrays) or spectral CT examinations with conventional techniques such as e.g. dual-source CT, kV switching, use of a dual-layer detector or use of the photon-counting detector, and calculation of monoenergetic images with conventional techniques, e.g. two-material decomposition into the components contrast medium (e.g. iodine) and soft tissue. Depending on the energy of the calculated monoenergetic CT images, the CT value of the contrast medium changes in these images, with iodine for example the CT value increases sharply with the decreasing energy of the monoenergetic images.

For the first preferred solution it is proposed, for patient-dependent optimization/reduction of the contrast medium amount for a standard single-energy CT scan for all or for selected available x-ray voltages, to calculate individually for the patient how the CT value of a predetermined contrast medium (e.g. iodine) would change relative to the CT value of this contrast medium at the reference tube voltage of the selected reference scan protocol (such a reference scan protocol can e.g. be a standard abdomen protocol at 120 kV).

The change of CT value on transition from the reference voltage to other tube voltages depends on the irradiated patient cross-section, which can be determined for example from an overview recording (topogram) preceding the CT examination. Starting from this e.g. percentage change of the CT value of the contrast medium on transition from a reference tube voltage to other tube voltages, a calculation is made as to how the administered contrast medium amount can be changed on transition to other tube voltages in order to obtain the same image contrast from organs filled with contrast medium as during an examination with the reference voltage. As explained in greater detail below, this can be done analytically or with the aid of empirical conversion factors. A proposal for changing the contrast medium amount on transition from a reference tube voltage to other tube voltages is notified to the user, e.g. at the operator interface of the CT scanner.

For the second preferred solution it is proposed, for patient-dependent optimization/reduction of the contrast medium amount in a dual-energy CT scan, that for all or selected available energies of a monoenergetic image, the calculation be performed for an individual patient as to how the CT value of a predetermined contrast medium (e.g. iodine) would change relative to the CT value of this contrast medium at the reference tube voltage of the selected reference scan protocol (such a reference scan protocol can e.g. be a standard abdomen protocol at 120 kV), or relative to a selectable reference energy (e.g. 70 keV).

Starting from this e.g. percentage change of the CT value of the contrast medium, on transition to the individual energies of monoenergetic images, it is calculated how the administered contrast medium amount can be changed in order to obtain the same image contrast from organs filled with contrast medium as during an examination with the reference voltage (or the reference energy). This can be done analytically or with the aid of empirical conversion factors. A proposal for a change of the contrast medium amount on transition to other energies of the monoenergetic images is notified to the user e.g. at the operator interface of the CT scanner.

At least one embodiment of the inventive device includes at least the following features:
a) An interface for provision of patient-specific data, which contains at least information about a patient cross-section relevant during the imaging measurement,
b) A CT value establishing unit for establishing expected CT values of a predetermined contrast medium for at least one region of interest of the patient at different candidate settings of an x-ray source arrangement and/or an image reconstruction device for reconstruction of monoenergetic image data from multi-energy measurements relative to a CT value for this region of interest at a reference setting of the x-ray source arrangement and/or the image reconstruction device as a function of the patient-specific data,
c) A contrast medium amount determination unit for determining in each case a relative candidate contrast medium amount for the different candidate settings which would lead to a CT value of the contrast medium which corresponds to the CT value of the contrast medium at the reference setting of the x-ray source arrangement and/or image reconstruction device, and
d) A display unit for displaying an optimum relative candidate contrast medium amount and the associated candidate setting.

Furthermore, at least one embodiment of the present invention also protects a control and processing unit for an x-ray imaging device, especially computed tomography device, operating in accordance with the aforementioned method and/or containing the aforementioned device.

Furthermore, at least one embodiment of the present invention also protects an x-ray imaging device, especially computed tomography device, operating in accordance with the aforementioned method and/or containing the aforementioned control and processing unit.

In particular major parts of at least one embodiment of the inventive device, e.g. the interface, the CT value establishing unit and the contrast medium amount determination unit can also be embodied in the form of software components.

At least one embodiment of the invention thus also includes a computer program which is able to be loaded directly into a memory of a control and processing unit of an x-ray imaging device, especially a computed tomography device, with program code in order to perform all steps of the inventive method when the program is executed in the control and processing unit. The control and processing unit in such cases can especially also be constructed as a system of a number of network computers or processors. A software realization has the advantage that existing x-ray imaging devices or computed tomography devices realized with suitable programmable processors and memories can be modified in a suitable manner by implementation of the program in order to operate in the inventive manner.

Further especially advantageous embodiments and developments of the invention emerge from the dependent claims as well as the description given below, wherein the independent claims of one claim category can be developed similarly to the dependent claims of another claim category. Likewise individual features or groups of features of different example embodiments of the invention can also be combined into new example embodiments.

In a preferred form of embodiment of the inventive method, the patient-specific data which contains information about a patient cross-section relevant for the imaging measurement is determined on the basis of previous x-ray-based (imaging) measurements, preferably from a topogram of the patient.

As an alternative, analog or digital photography or other image or video data can be employed for determining patient-specific data.

As an alternative previously measured and/or calculated patient-specific, especially anatomical data, can be included such as e.g. weight, age, gender, BMI value, extent of head, chest, midriff, hips, stomach, arms, legs, etc.

Naturally any given combination of the previously described patient-specific data can also be employed as anatomical data.

In a further preferred form of embodiment of the inventive method, the candidate setting of the x-ray source arrangement and/or of the image reconstruction device includes an x-ray source energy to be set at an x-ray radiation source, i.e. the x-ray voltage in kV and/or an x-ray radiation energy value in keV for the monoenergetic image data and/or the x-ray radiation dose, i.e. the x-ray current in A.

In a further preferred form of embodiment of the inventive method the CT values of the predetermined contrast medium to be expected are determined for different candidate settings relative to a CT value at the reference setting on the basis of the empirically-determined conversion factors (which have then been stored for example in a look-up table) and/or conversion functions and/or analytically. The CT values to be expected can therefore also be obtained from a database of discrete values or as a mathematical function.

The empirically-determined conversion factors and/or conversion functions are based in particular on phantom measurements. These types of phantom measurements can be carried out using standard bodies containing contrast media, e.g. cylinders or cubes, but also tissue substitute containing CM, such as gelatin or silicon material.

Preferably in such cases a plurality of measurements with different phantoms can be carried out, which each represent different models for different patient types (for example characterized in accordance with age group (adult/child), gender, different physiognomies (normal, fat, thin, muscular etc.) and/or different examination protocols for measurement tasks (such as lung examination, upper leg examination etc.). In this way a database with empirical conversion factors can be set up, or through different mathematical methods (such as fit methods and the like) conversion factors can also be determined. Missing values in such cases can also be interpolated or extrapolated if necessary.

A development of at least one embodiment of the inventive method and of at least one embodiment of the inventive device features an automatic setting of the x-ray energies E/keV or x-ray voltages U/kV and optional x-ray currents I/A belonging in the inventive manner to the optimum contrast medium amount.

A development of at least one embodiment of the inventive method and of at least one embodiment of the inventive apparatus features an automatic application of the amount of the specified contrast medium or of the contrast medium mixture with the previously determined optimum, especially minimum, concentration in an applicator.

A preferred form of embodiment of an x-ray-based imaging device or of a computed tomography device, in addition to the inventive apparatus, has at least the following components:

An x-ray tube for creating a bundle of x-rays with an energy spectrum for scanning the patient, A detector for measuring the attenuation of the x-ray radiation on its passage through the patient, A control and processing unit for controlling the apparatus and creating the x-ray presentations of the patient with the aid of stored and executed computer programs, wherein An adjustment device has different operating parameters at least in relation to the x-ray energies E/keV or x-ray voltages U/kV (and optionally x-ray currents I/A) used, A display device, which after the direct or indirect input of patient parameters (e.g. examination volume and tissue structure), at least displays a combination of type of contrast medium or the contrast medium mixture, its minimum concentration and patient-dependent absolute amounts needed, as well as the assigned x-ray energy E/keV or x-ray voltages U/kV (and optionally x-ray currents I/A) for the (subsequent) examination.

If in particular a single-energy-CT scan is undertaken with at least one embodiment of the inventive method or at least one embodiment of the inventive apparatus, the following advantageous developments are proposed:

In a further configuration stage, in addition to the changed amount of contrast medium for each tube voltage, a correspondingly changed tube current, e.g. for retaining the same image noise, is also calculated and notified to the user.

In a further version the system calculates whether, taking into account the performance limits of specific scanner components (e.g. x-ray tube or voltage generator for the x-ray voltage) the CT scan can be carried out at the modified tube voltage.

In a further version a tube voltage is proposed to the user, taking into account the performance limits of specific scanner components, with which the lowest possible amount of contrast medium can be achieved for the planned examination and the specific patient.

If in particular a dual-energy CT scan is undertaken with the inventive method or the inventive apparatus, the following advantageous developments are proposed:

In a further version an energy of the monoenergetic images is proposed to the user with which he can achieve the lowest possible contrast medium amount for the planned examination and the specific patient.

In a further embodiment it is proposed that, for minimizing/optimizing the total contrast medium amount for the patient, different contrast media are taken into account and the amount to be administered for achieving a predetermined corresponding contrast relative to a reference (e.g. iodine CT value at the reference tube voltage & reference scan protocol) is determined as a function of the indication and the patient geometry (especially attenuation). A corresponding proposal for optimum contrast medium should be notified to the user before the scan at the operator interface of the CT scanner.

An embodiment of the inventive CT system, in its basic configuration for example, can involve a conventional CT system with a single x-ray source/detector system (single-source system) wherein the x-ray tube used at least possesses the option of influencing the energy spectrum of the x-ray radiation used. This can be done for example by controlling the acceleration voltage or the insertion of filters into the beam path. Such systems are generally known.

It is pointed out in this context that basically any known CT systems which have the opportunity of influencing the energy spectrum of the x-ray or braking radiation used, can be adapted in accordance with an embodiment of the invention.

Figure 1:
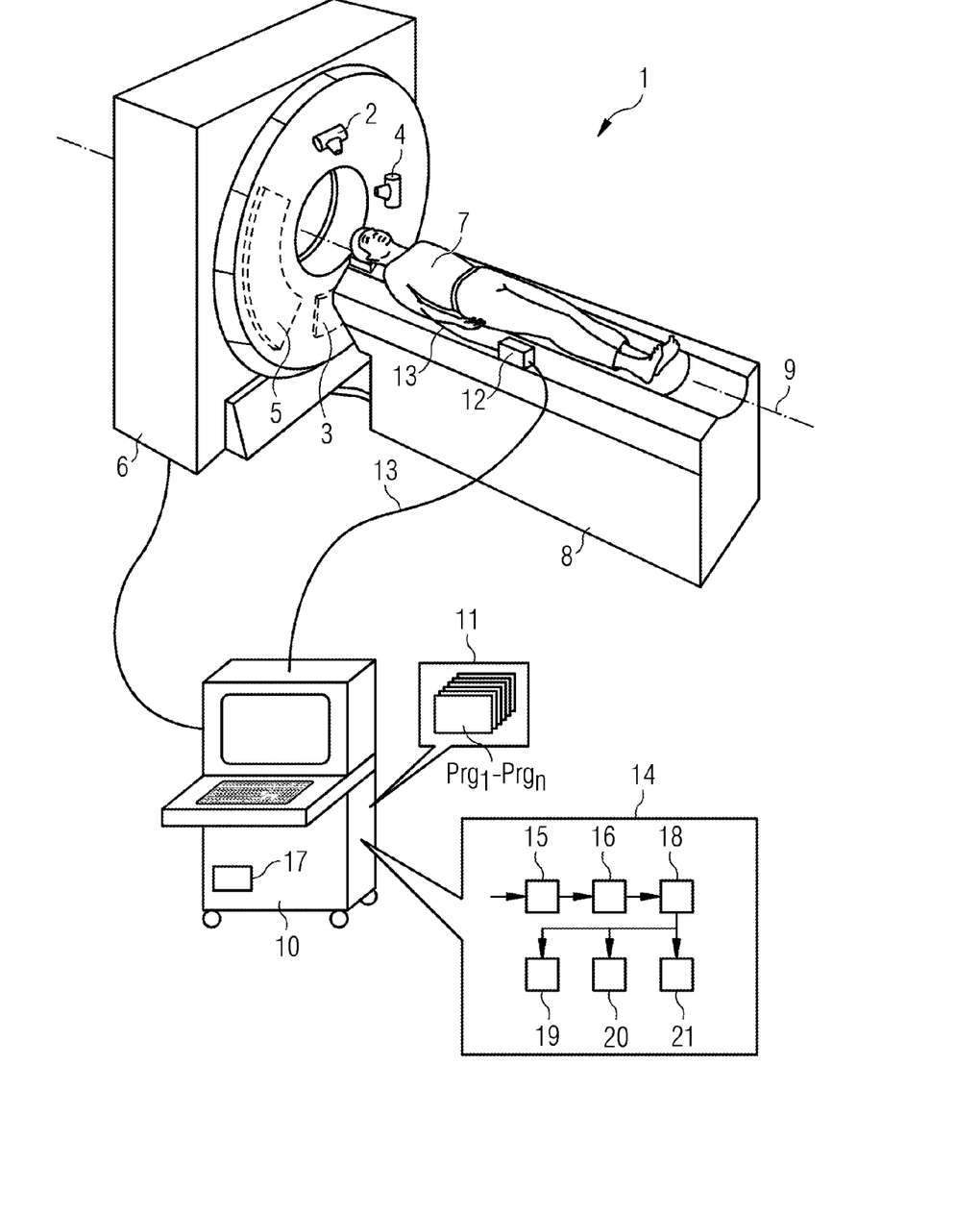
The FIGURE shows an inventive computed tomography device (also called a CT system below) with an inventive apparatus, operating with an embodiment of the inventive method for patient-dependent optimization and reduction of the contrast medium amount.

For example a dual-source system can also be used, as is shown in the FIGURE, or even a system with more than two x-ray sources. Such a dual-source CT system 1 has a first x-ray tube 2 with a detector 3 lying opposite it and a second x-ray tube 4 with a further detector 5 lying opposite it. Both x-ray source/detector systems 2, 3 and 4, 5 are disposed in the gantry housing 6 on a gantry rotating around a system axis 9 and not shown visibly here. The patient 7 is located on a patient couch 8 able to be moved longitudinally, which is pushed for scanning the patient 7 during the rotation of the x-ray source/detector system continuously or in stages through an opening in the gantry housing 6. By this process the patient 7 is scanned in a spiral shape or in the shape of multiple circles.

Before or during the scanning of the patient 7, to improve the contrast of a CT representation reconstructed from the detector output data, a contrast medium is applied to the patient 7. This can be done for example by a contrast medium injector 12, which injects the selected contrast medium with a predetermined flow, if necessary also with time-dependent variation, into the patient 7 via an injection line.

The contrast medium can for example be embodied for a cardiac examination such that, after its injection, it remains (almost) exclusively in the blood vessels before it is broken down. This enables a very good presentation of the blood vessels and corresponding clinical evaluations. However a contrast medium can also be used, which as a tumor marker is applied specifically to tumor tissue and highlights said tissue accordingly. This tumor is greatly accentuated during the CT examination by this and is thus easily able to be diagnosed or defined in its position and extent. Combinations of the two previously described variants are also possible for example, wherein then preferably different contrast-forming elements can be used, which as a result of their energy-specific different absorption behavior, can be shown separately.

The overall CT system 1 can be controlled and if necessary the detector data and reconstruction of the CT presentations as slice images or volume data can be evaluated by a control and processing unit 10. For reconstruction of the image data from the measured raw data (i.e. from the projection data acquired with the x-ray source/detector systems 2, 3 and 4, 5) the control and processing unit 10 especially also has a reconstruction unit 17. Inter alia this reconstruction unit can be embodied so that for example it includes a specific image combination unit (not shown) in order, on the basis of raw data which has been acquired with different x-ray energies, and/or on the basis of image data based thereon in each case for different x-ray energies, to create mixed images which correspond to monoenergetic images for a predetermined (virtual) x-ray energy. This control and processing unit 10 has a memory 11, in which, as well as the measured detector data, computer programs Prg1-Prgn are also stored, which are executed during operation and essentially handle the control of the system and the evaluation of the data.

Furthermore it is pointed out in this context that it is also part of the invention for the CT system to be linked to a number of processor systems and for individual processing steps to take place locally in other processing units.

The use of a dual or multiple x-ray source/detector system in accordance with the FIGURE offers a variety of advantages compared to a conventional CT system. Thus for example different detectors can be used with different modes of operation if detectors are not available which are able to be switched over into different modes of operation with the same configuration. In addition a pre-scan or the actual scan can be carried out simultaneously with each x-ray source/detector system with different energy spectrum in each case. Likewise a simple simultaneous recording of a number of topograms for determining the patient dimensions is possible, which facilitates a later optimum choice of the correct contrast medium/radiation combination.

The control and processing unit 10 contains an embodiment of the inventive apparatus 14 for patient-dependent optimization and reduction of the contrast medium amount, especially operating in accordance with an embodiment of the inventive method.

The apparatus 14 contains an interface 15 for provision of patient data, e.g. about a patient cross-section to be irradiated, which contains the ROI to be examined. This interface 15 can be a simple interface for transferring the finished data but can also be a software module for example, which accepts and evaluates a previously created topogram of the current patient and in doing so, determines the patient cross-section to be irradiated in the subsequent examination.

This patient data or the patient cross-section are then forwarded to a CT-value determination unit 16 of the apparatus 14 for determining CT values of a contrast medium to be expected at different candidate settings of the x-ray sources relative to a CT value at a reference setting of the x-ray sources, e.g. 120 kV, as a function of the patient data.

As an alternative or in addition, the CT value establishing unit 16 can be embodied so that it determines the CT values to be expected as a function of the patient data or the patient cross-section if the image reconstruction device 17 reconstructs monoenergetic image data from preceding multi-energy measurements for different candidate settings, i.e. for different virtual energies, relative to a CT value for this ROI at a reference setting, e.g. 70 kV and 140 kV.

This information about the relative change of the CT values for different candidate settings, especially here "real" or "virtual" candidate x-ray energy values, is then transferred to a contrast medium amount determination unit 18 of the apparatus 14, which in each case determines a relative candidate contrast medium amount for the different candidate settings which would lead to a CT value of the contrast medium which corresponds to the CT value of the contrast medium at the reference setting of the x-ray sources.

For example it is determined here that, with a use of a "real" or "virtual", x-ray energy of 40 keV, corresponding to a tube voltage of 70 kV, instead of the energy used in most cases of 70 keV, corresponding to a tube voltage of 120 kV (which in this case also represents the reference value) the amount of contrast medium can be reduced by 30%.

Provided an absolute contrast medium amount is already predetermined in any event for a specific examination with the reference energy concerned in an examination or control protocol, as an alternative the absolute value of the contrast medium amount needed can naturally also be determined during a measurement with the modified settings.

The apparatus 14 also contains a display unit 19 for displaying an optimum relative or absolute candidate contrast medium amount thus determined and the associated candidate setting of the x-ray sources, e.g. x-ray voltage and if necessary x-ray current. This display unit 19 can for example involve a suitable software unit which activates a display of the control and processing unit 10 in a suitable manner.

In particular a query can also be sent to an operator in this way as to whether he is in agreement with the proposed setting values. I.e. the proposed setting value is output, for example, and the apparatus then waits for a confirmation signal or a modification signal of a user interface.

The apparatus 14 here also contains a setting device 20, by means of which (for example after a confirmation by the operator), based on the established optimum setting values, an automatic setting of the determined x-ray energies or x-ray voltages and optional x-ray currents of the x-ray sources 2, 4 is then undertaken. This setting device 20 can also be embodied in the form of a software module. For example the corresponding values in the control protocols can be modified for the subsequent measurement by said device.

Likewise the apparatus 14 can finally include a filling device 21, by means of which the applicator 12 is filled automatically with the established optimum amount of the determined contrast medium.

In conclusion it is pointed out once again that the field distribution correction elements described above in detail merely involve exemplary embodiments which can be modified by the person skilled in the art in a wide diversity of ways, without departing from the field of the invention. Furthermore the use of the indefinite article "a" or "an" does not exclude the features concerned also being able to be present multiple times. Likewise the term "unit" and "module" do not exclude the components concerned comprising a number of interacting sub-components, which if necessary can also be spatially distributed.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for patient-dependent determination of a contrast medium amount before an x-ray-based imaging measurement for creating image data of a patient, the method comprising:

provisioning patient-specific data, the patient-specific data including at least information about a patient cross-section relevant for the x-ray-based imaging measurement;

establishing at least one of expected CT values or expected CNR values of a contrast medium for at least one region of interest of the patient at different candidate settings for at least one of an x-ray source arrangement or an image reconstruction device for reconstruction of monoenergetic image data from multi-energy measurements, relative to a CT value or a CNR value for the at least one region of interest at a reference setting for the at least one of the x-ray source arrangement or the image reconstruction device as a function of the patient-specific data;

determining a candidate contrast medium amount for different candidate settings which would lead to a CT value or a CNR value of the contrast medium which corresponds to the CT value or the CNR value of the contrast medium at the reference setting for the at least one of the x-ray source arrangement or the image reconstruction device; and displaying an optimum candidate contrast medium amount and associated candidate setting.

2. The method of claim 1, wherein the patient-specific data is established based on the previous x-ray-based imaging measurements.

3. The method of claim 1, wherein a candidate setting for the at least one of the x-ray source arrangement or the image reconstruction device includes at least one of an x-ray radiation energy or an x-ray radiation energy value for the monoenergetic image data.

4. The method of claim 1, wherein a candidate setting for the x-ray source arrangement includes an x-ray radiation dose.

5. The method of claim 1, wherein the establishing establishes the at least one of the expected CT values or the expected CNR values at different candidate settings relative to the CT value or the CNR value at the reference setting based on at least one of empirically-established conversion factors or conversion functions.

6. The method of claim 5, wherein the at least one of empirically-established conversion factors or conversion functions are based on phantom measurements.

7. The method of claim 4, further comprising:
automatically setting at least one of an x-ray energy or an x-ray current for a subsequent x-ray-based imaging measurement based on the associated candidate setting associated with the optimum candidate contrast medium amount.

8. The method of claim 1, further comprising:
filling an applicator with an amount of a contrast medium based on the optimum candidate contrast medium amount.

9. A non-transitory computer program product, loadable directly into a memory of a control and processing unit of an x-ray imaging device, the non-transitory computer program product including program code sections that, when executed by the control and processing unit, cause the x-ray imaging device to perform the method of claim 1.

10. The method of claim 2, wherein the patient-specific data is established from a topogram of the patient.

11. The method of claim 2, wherein a candidate setting of the at least one of the x-ray source arrangement or the image reconstruction device includes at least one of an x-ray radiation energy or an x-ray radiation energy value for the monoenergetic image data.

12. The method of claim 2, wherein the establishing establishes the at least one of the expected CT values or the expected CNR values at different candidate settings relative to the CT value or the CNR value at the reference setting based on at least one of empirically-established conversion factors or conversion functions.

13. The method of claim 12, wherein the at least one of empirically-established conversion factors or conversion functions are based on phantom measurements.

14. A control and processing unit for an x-ray imaging device, operating in accordance with the method of claim 1.

15. An apparatus for patient-dependent determination of a contrast medium amount before an x-ray-based imaging measurement for creating image data of a patient, the apparatus comprising:
 an interface to provision patient-specific data, the patient-specific data including information about a patient cross-section relevant for the x-ray-based imaging measurement;
 at least one processor configured to execute computer-readable instructions to
  establish at least one of expected CT values or expected CNR values of a contrast medium for at least one region of interest of the patient at different candidate settings for at least one of an x-ray source arrangement or an image reconstruction device for reconstruction of monoenergetic image data from multi-energy measurements, relative to a CT value or a CNR value for the at least one region of interest at a reference setting of the at least one of the x-ray source arrangement or the image reconstruction device as a function of the patient-specific data;
  determine a candidate contrast medium amount for the different candidate settings which would lead to a CT value or a CNR value of the contrast medium which corresponds to the CT value or the CNR value of the contrast medium at the reference setting for the at least one of the x-ray source arrangement or the image reconstruction device; and
 a display to display an optimum candidate contrast medium amount and associated candidate setting.

16. The apparatus of claim 15, wherein the at least one processor is further configured to execute computer-readable instructions to automatically set at least one of an x-ray energy and an x-ray current based on the associated candidate setting associated with the optimum candidate contrast medium amount.

17. The apparatus of claim 15, further comprising:
 a filling device to automatically fill an applicator with an amount of contrast medium based on the optimum candidate contrast medium amount.

18. A control and processing unit for an x-ray imaging device, comprising the apparatus of claim 15.

19. An x-ray imaging device, comprising the control and processing unit of claim 18.

20. The apparatus of claim 16, further comprising:
 a filling device to automatically fill an applicator with an amount of contrast medium based on the optimum candidate contrast medium amount.

* * * * *